United States Patent [19]

Tomes et al.

[11] Patent Number: 5,322,783
[45] Date of Patent: Jun. 21, 1994

[54] SOYBEAN TRANSFORMATION BY MICROPARTICLE BOMBARDMENT

[75] Inventors: Dwight Tomes, Cumming; Dennis Bidney; Charisse M. Buising, both of Des Moines, all of Iowa

[73] Assignee: Pioneer Hi-Bred International, Inc., Des Moines, Iowa

[21] Appl. No.: 422,875

[22] Filed: Oct. 17, 1989

[51] Int. Cl.$^5$ .............................................. C12H 5/14
[52] U.S. Cl. .............................. 435/172.1; 435/172.3; 435/240.4; 800/205; 800/DIG. 26
[58] Field of Search ............... 435/172.1, 172.3, 240.4; 935/52.67; 800/205, DIG. 26

[56] References Cited

U.S. PATENT DOCUMENTS 4,945,050  7/1990  Sanford et al. .................. 435/172.1

OTHER PUBLICATIONS

McCabe et al (Aug. 1988) Bio/Technology 6:923–926.
Wang et al (1988) Plant Molecular Biology 11:433–439.
Meyer et al (1985) Mol. Gen Genet 201: 513–518.
Potrykus (Jun. 1990)) Bio/Technology 8: 535–538.

Primary Examiner—Che S. Chereskin
Attorney, Agent, or Firm—Pioneer-Hi Bred International, Inc.

[57] ABSTRACT

Plant cells in tissue culture are more efficiently transformed in a method which involves treatment with a cytokinin followed by incubation for a period sufficient to permit undifferentiated cells in cotyledonary node tissue to differentiate into meristematic cells and to permit the cells to enter the phases between the G1 and division phases of development.

9 Claims, No Drawings

SOYBEAN TRANSFORMATION BY MICROPARTICLE BOMBARDMENT

BACKGROUND OF THE INVENTION

This invention relates to the transformation of plant cells, and particularly to improved methods for the transformation of intact plant cells in tissue culture.

Much research in plant molecular biology is now directed to the improvement of plant varieties via use of recombinant DNA techniques. Historically, plant breeders used classical genetic techniques to identify, preserve and crossbreed varietal lines having desirable traits. More recently, new plant varieties were induced by chemicals or by radiation treatment to mutate plant cells which were then regenerated using tissue culture techniques. These random and unpredictable approaches have obvious drawbacks. By the use of recombinant DNA technology, specific genes producing specific proteins, such as those imparting insect resistance, may be introduced into a plant to produce a desired variety with a particular trait. One method for the introduction of recombinant DNA into plant cells is the microparticle bombardment method described by Sanford et al., *Journal of Particle Science and Technology*, 5:27–37, the disclosures of which are hereby incorporated herein by reference.

In the transformation of cells by microparticle bombardment introduction of recombinant DNA to impart a desired trait, it is important that the transformation be efficient, i.e., that large numbers of cells be transformed by the method, at least transiently, so that the function and effectiveness of the structural gene of interest and/or the regulatory sequences associated with the structural gene of interest can be evaluated by conventional analytical methods. In the past, efficiency of transformation of some cell lines, such as soybean tissue culture cells, has been undesirably low, so that gene products were not formed in sufficient amounts to be analyzed quantitatively by simple methods. Several different treatments were tried to increase the level of transient .gene activity. These have included treatment with various plant hormones, use of different cultivars of soybeans, and use of different transformation vectors. Disadvantages with each of these approaches continued to be low transient gene activity and a high degree of variability from experiment to experiment.

DISCLOSURE OF THE INVENTION

It has now been determined that treatment of plant tissue culture cells prior to microparticle bombardment has a large effect on their susceptibility to transformation. In particular, in the transformation of excised soybean meristems, it has now been found that it is important to pretreat the cells in a medium containing a cytokinin, followed by an additional period of culturing after cytokinin treatment to allow the cells to become synchronized in their reproductive cycles and to reach a phase of optimal susceptibility to transformation.

"Cytokinin" is used herein as a generic term for the class of plant hormones which promote cytokinesis and shoot formation in cultured plant cells and serve functions similar to kinetin [6-(furfurylamino)purine] or zeatin [6-(4-hydroxy-3-methyl-2-butenyl)aminopurine. This term thus also encompasses synthetic analogs of naturally occurring cytokinins, hundreds of which are known in the art. The most effective of these are generally the $N^6$-substituted adenine derivatives. A preferred compound is benzylaminopurine (BAP).

The plant meristem tissue is generally treated with cytokinin for a period of from about 12 to about 24 hours. A 24 hour treatment is effective and convenient and is preferred. Longer treatment periods do not appear to further enhance the efficiency of transformation. A preferred method of treatment is to place the excised tissue in a medium containing the cytokinin. When BAP is used it is preferably incorporated in the medium at a concentration of from about 0.1 mg/L to about 10 mg/L. Lower concentrations of from about 0.1 to about 0.5 mg/L have been found to be useful in the transformation of sunflower tissues, while higher concentrations of from about 2 mg/L to about 10 mg/L have been found useful in the transformation of soybean meristem tissues. In general, the concentration should be sufficient for the cytokinin to exert its usual hormonal effects on the plant tissues.

While not intending to be limited by theory, it appears that the treatment with cytokinin in the method of this invention interrupts division of the cells of the primary apical meristem for a period sufficient for the undifferentiated cells located at the cotyledonary node to differentiate into meristematic cells. This occurs because normal apical dominance is effectively suspended, for a period of from about 48 to about 72 hours. When this occurs, the other undifferentiated cells can become active and begin to differentiate, which would not otherwise occur. Thus, this treatment can be described as having the net effect of synchronizing the time at which the cells enter the G1 and the division phases of development, so that when the cells are subjected to microparticle bombardment, more of the cells are in the optimal phase for transformation. Anatomical studies also show that the phenotype of the cells of the surface are changed such that meristematic cells which are capable of division are present at the outermost layers, which are accessible to the microparticle bombardment. In this method the plant tissues are manipulated in a way which synchronizes the cell division process among the cells of the target tissue and promotes its responsiveness and sensitivity to the transforming recombinant DNA.

Thus, following treatment, the meristem tissue is incubated for a period sufficient to permit undifferentiated cotyledonary node cells to differentiate into meristem cells, and preferably for a large number of the cells to enter the desired phases between the G1 phase and the division phase prior to bombardment. Most preferably, the differentiated meristematic cells will be in the S phase at the time of bombardment. Depending upon the species, this can take from about 12 hours to about 72 hours. In soybean meristem transformation, approximately 48 hours is required after treatment. In any event, however, this period can readily be determined for any selected species and tissues by including in the process a number of control specimens which can be sectioned and examined microscopically at regular intervals for the above-described changes (differentiation of cotyledonary node cells into meristematic tissue, entry of large numbers of cells into the G1, S and division phases) to determine the optimum time for bombardment. These phases of the cell cycle will be well known to and easily recognized by plant cell biologists. The G1 phase is the phase immediately prior to DNA replication. It is recognized by 1x amount of DNA within the cells. The S phase is the phase of DNA replication, wherein the amount of DNA within the cells doubles. The division (M) phase is the phase of physical reorganization of the genetic material and physical division of the cell into two daughter cells, each of which contains 1x amount of DNA. S phase can also be identified by the propensity of cells to incorporate radiolabled nucleotides. The incubation is done using conventional conditions of medium, light, and temperature.

In a preferred embodiment of the method of this invention, meristems are dissected from imbibed soybean seeds and are then pretreated in a medium containing 5 mg/L benzylaminopurine (BAP) for 24 hours. Following BAP treatment, the meristems are placed on a ½ strength Murashige-Skoog (MS) base culture medium containing 1% sucrose for an additional 24 hours. On the third day (2 days after cytokinin treatment), the exposed meristematic area is treated with microparticle bombardment. The typical result of bombardment on day 3 after excision (day 2 after cytokinin treatment) is that expression is at least one order of magnitude greater that bombardment immediately after subculture or without cytokinin treatment.

This method offers advantages in transformation of soybean cells because it allows transformation of substantially any soybean variety, rather than only those cultivars, such as Peking, which are commonly known to be easily transformed but which are also known to have poor agronomic characteristics. In addition, since having greater numbers of cells at the appropriate phase of development for transformation is desirable in transformation of any plant species, this invention offers an improved method of transformation of other difficult to transform crop species such as maize (corn), wheat, canola, millet, alfalfa, sorghum and rice.

Having now generally described this invention, the same will be better understood by reference to the following specific example, which is included herein for purposes of illustration only, and is not intended to be limiting unless otherwise specified. All percentages herein are by weight unless otherwise indicated.

EXAMPLE

On day 0 of the experiment soybean seeds of a proprietary cultivar known as Xb35b (Pioneer Hi-Bred International, Biotechnology Research Department, 7300 N.W. 62nd Ave., Johnston, Iowa) were surface sterilized with a 10% v/v solution of Clorox in water and soaked overnight in a 0.25M sorbitol solution.

On day 1 of the experiment (the following morning), the unifoliates (pumules) and trifoliate primordia were excised and removed. These were arranged in a petri dish on MS base medium containing 5 mg/L benzylamino purine (BAP). On the same day, one group of explants were subjected to microparticle bombardment using the method described in Tomes, U.S. patent application Ser. No. 351,075, filed May 12, 1989. The explants were bombarded three times with particles carrying the pPHI413 vector of Beach et al. (Pioneer Hi-Bred International Biotechnology Research Department) which carries a beta-D-glucuronidase (GUS) gene to provide a visual and analyzable transformation marker, and placed in a dark room at 28° C.

On day 2, another group of excised embryos were bombarded in the same manner. These were placed on shoot regeneration medium (MS base medium with 1% sucrose) and incubated in light at 28° C.

On day 3, yet another group of explants were bombarded and incubated in the same manner as the second group.

On day 4, a transient GUS assay was performed on each of the groups using two meristems per sample. Results were as shown in the following tables:

TABLE 1

| Bombardment Schedule | | | | | | % GUS Protein ($10^{-4}$) | | |
|---|---|---|---|---|---|---|---|---|
| Day 1 | Day 2 | Day 3 | Total | N | N+ | Min | Mean | Max |
| 3× | — | — | 3× | 8 | 0 | — | — | — |
| — | 3× | — | 3× | 14 | 5 | 1.7 | 2.9 | 4.3 |
| — | — | 3× | 3× | 6 | 6 | 8.2 | 42.1 | 117.5 |
| 3× | 3× | — | 6× | 8 | 1 | 3.5 | 3.5 | 3.5 |
| 3× | 3× | 3× | 9× | 2 | 2 | 1.5 | 2.1 | 2.7 |

N = total number of samples
N+ = number of samples with positive GUS assay

These results suggest that the treatment method of this invention is more valuable than additional bombardments in producing transient transformation with high efficiency.

What is claimed is:

1. An improved method for transforming the cells of soybean tissue comprising cotyledonary node cells in tissue culture via microparticle bombardment, comprising the steps of
   a. treating the tissue with a cytokinin; and
   b. incubating the treated tissue for a period sufficient to permit the cotyledonary node cells in the tissue to differentiate into meristematic tissue cells prior to bombardment.

2. A method according to claim 1 wherein the tissue subjected to the method is excised meristem tissue.

3. A method according to claim 2 wherein the meristem is excised from an imbibed seed.

4. A method according to claim 1 wherein the cytokinin is benzylaminopurine.

5. A method according to claim 4 wherein the benzylaminopurine is incorporated in culture medium at a concentration of from about 0.1 mg/L to about 10 mg/L.

6. A method according to claim 1 wherein the tissue is treated for a period of from about 12 hours to about 24 hours.

7. A method according to claim 1 wherein the tissue is incubated for a period of from about 24 hours to about 3 days after cytokinin treatment and prior to bombardment.

8. A method according to claim 1 wherein the differentiated meristematic cells are in phases from the G1 phase to the division phase prior to bombardment.

9. A method according to claim 10 wherein the differentiated meristematic cells are in the S phase at the time of bombardment.

* * * * *